US008221471B2

(12) United States Patent
Kovach et al.

(10) Patent No.: US 8,221,471 B2
(45) Date of Patent: Jul. 17, 2012

(54) PEDICLE SCREW FIXATION SYSTEM (75) Inventors: Matthew Kovach, Alburtis, PA (US);
Paul Weaver, Douglassville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 607 days.

(21) Appl. No.: 11/753,161

(22) Filed: May 24, 2007

(65) Prior Publication Data

US 2008/0294203 A1  Nov. 27, 2008

(51) Int. Cl.
*A61B 17/70* (2006.01)
(52) U.S. Cl. ........................................ 606/266
(58) Field of Classification Search ........... 606/272, 606/246, 308, 305, 301, 264–268, 270, 277–279, 606/295, 302, 304, 311, 312, 315, 317
See application file for complete search history.

(56) References Cited

U.S. PATENT DOCUMENTS

| 5,562,663 | A | 10/1996 | Wisnewski et al. |
| 5,624,442 | A | 4/1997 | Mellinger et al. |
| 2004/0162560 | A1 | 8/2004 | Adams |
| 2004/0193160 | A1 | 9/2004 | Richelsoph |
| 2005/0277924 | A1 | 12/2005 | Roychowdhury |
| 2005/0283157 | A1* | 12/2005 | Coates et al. ............ 606/73 |
| 2006/0149233 | A1 | 7/2006 | Richelsoph |
| 2006/0149241 | A1 | 7/2006 | Richelsoph et al. |
| 2006/0161153 | A1* | 7/2006 | Hawkes et al. .......... 606/61 |
| 2006/0241616 | A1* | 10/2006 | Konieczynski et al. ..... 606/69 |
| 2007/0118125 | A1* | 5/2007 | Orbay et al. ............ 606/69 |
| 2008/0015597 | A1* | 1/2008 | Whipple ................. 606/73 |
| 2008/0083613 | A1* | 4/2008 | Oi et al. ................. 204/237 |
| 2008/0097441 | A1 | 4/2008 | Hayes et al. |
| 2008/0215100 | A1* | 9/2008 | Matthis et al. ........... 606/305 |
| 2009/0030457 | A1* | 1/2009 | Janowski et al. ........ 606/246 |

FOREIGN PATENT DOCUMENTS

| EP | 1 364 622 | 11/2003 |
| WO | WO 2004/089245 | 10/2004 |
| WO | WO 2006/116437 | 11/2006 |
| WO | WO 2007/122494 | 11/2007 |

OTHER PUBLICATIONS

European Search Report for European App. No. 08 15 3710, Mar. 12, 2009.

* cited by examiner

*Primary Examiner* — Eduardo C Robert
*Assistant Examiner* — Summer Kostelnik
(74) *Attorney, Agent, or Firm* — RatnerPrestia (57) ABSTRACT A locking mechanism for locking a rod in a screw and rod fixation assembly includes a cap having a sidewall and a locking element extending from at least a portion of the sidewall. Locking mechanism cooperates with a receiver component for a spinal fixation rod to lock the rod in the receiver without requiring application of torque. A method of locking a spinal fixation member in a receiver of a screw fixation assembly includes the steps of placing the spinal fixation member into a channel of a receiver, axially advancing a locking cap into the receiver toward the spinal fixation member without application of any torque, and securing the locking cap in a locked position above the spinal fixation member without application of any torque.

21 Claims, 10 Drawing Sheets

PEDICLE SCREW FIXATION SYSTEM

FIELD OF THE INVENTION

The invention relates to fixation systems for the spine, and more particularly to a screw fixation system with a locking mechanism that can be tightly secured without applying torque.

BACKGROUND OF THE INVENTION

Several techniques and systems have been developed for correcting and stabilizing the spine and for facilitating fusion at various levels of the spine. Stabilization of the spine for various conditions, including degenerative disk disease, scoliosis, spondylolisthesis, and spinal stenosis, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span a large number of vertebrae, such as three or four. The spine anatomy, however, rarely allows for three or more implants to be directly in line. In order to allow for this irregularity, the rod must be contoured to the coronal plane.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Another option is an implantation fixation system that locks a rod to several vertebrae. In these system, as with other spinal fixation systems, various fasteners, such as bone screws, are used to secure the implantation fixation assembly to the desired and targeted vertebrae of the patient. These screws vary in design and shape depending upon their desired location and use.

Polyaxial locking screws are frequently used as fasteners in implantation fixation systems. Once these screws are set in a desired position, the screws must be securely fixed in that position. Movement of the screw must be minimized or eliminated. This requires a fixation system that securely engages the polyaxial screw and minimizes or prevents movement of the screw.

There are numerous polyaxial screws and fixation systems existing in the market today. For example, U.S. Pat. No. 6,740,086 to Richelsoph (the '086 Patent) discloses a fixation system having a hollow fixing mechanism. The fixing mechanism has a central passage and a polyaxial screw inserted into the central passage. In a preferred embodiment, the screw has a head portion that seats inside one end of the hollow fixing mechanism, and a threaded shank that projects through the end of the fixing mechanism in an exposed manner. The fixing mechanism has wall portions that form channels for receiving a rod. The rod is seated in the channels and extends transversely through the central passage. The wall portions include internal threads along the passage for receiving a set screw. The set screw has an external thread that engages the internal threads in the passage. In this arrangement, the set screw can be threaded into the passage and advanced into the passage into engagement with a rod or rod seating mechanism to securely fix the polyaxial screw head to the fixing mechanism and rod.

The fixation system of the '086 Patent utilizes a threaded engagement, which provides a mechanical advantage analogous to an inclined plane. The threads provide a means of overcoming a large amount or axial resistance imparted by the rod. The mechanical advantage of the inclined plane creates large axial forces that compress the screw head and fixing mechanism together, forming a rigid construct. One drawback of this construct, and of all systems that utilize set screws or other rotating locking elements, is the requirement of torque to tighten the locking element. When the locking element is tightened through torque, the torque gradually transfers to the fixing mechanism and polyaxial screw. A significant amount of torque is typically applied in the final tightening. This introduces a substantial risk of "blowout", in which torque and/or other components of force tilt the shank out of its set alignment in the screw hole, causing the shank to break through the relatively thin bone wall of the pedicle. In such a case, removal and resetting of the polyaxial screw can exacerbate the trauma to the bone.

To control the risk of blowout, some practitioners use additional instrumentation to apply a countertorque to the fixation mechanism, so that the torque applied to set screw does not cause rotation or displacement of the fixing mechanism and polyaxial screw. This requires the careful balancing of torque with countertorque, and any imbalance can still cause blowout. Moreover, application of countertorque requires an additional instrument to be used at the same time that the set screw is being driven into the fixing mechanism. Aside from the obvious disadvantage of adding to instrument costs and instrument preparation, the countertorque instrument can be cumbersome to use while advancing the locking element at the same time. A surgeon who advances the set screw and holds the countertorque instrument at the same time will not have any hands free. This may compel the need for additional medical personnel during installation of the fixing assembly. The countertorque instrument further adds to the visual obstructions over the incision, and may require the size of the incision to be made larger to accommodate the additional instrumentation.

Systems that use threaded locking mechanisms are also difficult to use, requiring precise coordination and mating of components. In many cases, the assembly is very small, and proper thread starting can be difficult. If the threading is not started properly, the locking mechanism can bind, damaging the threaded surfaces and rendering the components unusable.

Accordingly, there is a need for a fixation mechanism or device that provides a strong and secure locking of the screw in its desired position, with minimal risk to the impacted bone area. Additionally, there is a need for a fixation mechanism or device that is not cumbersome to operate, and requires less instrumentation. Furthermore, there is a need for a fixation mechanism or device that more efficiently establishes a secure locking of the screw, with less time and effort required than prior systems and techniques.

SUMMARY OF THE INVENTION

The foregoing drawbacks and the needs to improve on known fixation systems and techniques are resolved to a large degree by a fixation system and locking mechanism in accordance with the present invention.

In a first aspect of the invention, a locking mechanism for locking a rod in a screw and rod fixation assembly includes a cap having a sidewall and a locking element extending from at least a portion of the sidewall, the locking element being deformable between a compressed condition, in which the locking element assumes a first cross-sectional dimension, and a relaxed condition, in which the locking element assumes a second cross-sectional dimension, the second cross-sectional dimension being larger than the first cross-sectional dimension.

In a second aspect of the invention, a spinal fixation assembly includes a receiver for a spinal fixation rod, the receiver having a hollow body. The hollow body includes a bore and a locking surface in the bore. A locking cap in the bore of the receiver has a sidewall and a rod engaging end. A locking element extends from the sidewall of the locking cap and engages the locking surface in the bore. The locking element is displaceable between a compressed condition and a relaxed condition. In the relaxed condition, the locking element engages the locking surface.

In a third aspect of the invention, a method of locking a spinal fixation member in a receiver of a screw fixation assembly includes the steps of placing the spinal fixation member into a channel of the receiver, axially advancing a locking cap into the receiver toward the spinal fixation member without application of any torque, and securing the locking cap in a locked position above the spinal fixation member without application of any torque.

BRIEF DESCRIPTION OF THE DRAWINGS

The foregoing summary and following description will be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
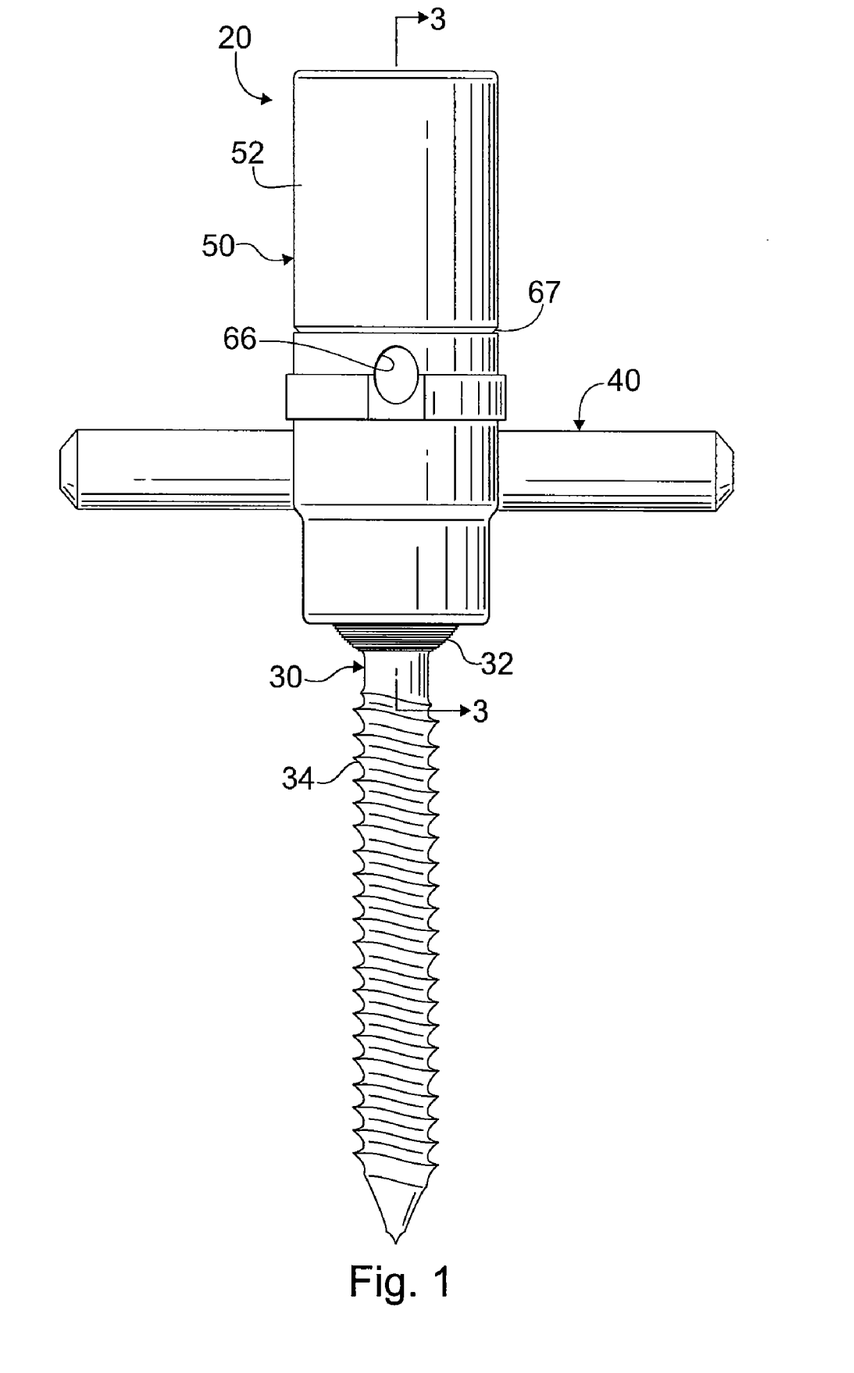
FIG. 1 is a perspective view of a screw and rod fixation assembly in accordance with a first exemplary embodiment of the present invention, viewed from a first perspective.
Figure 2:
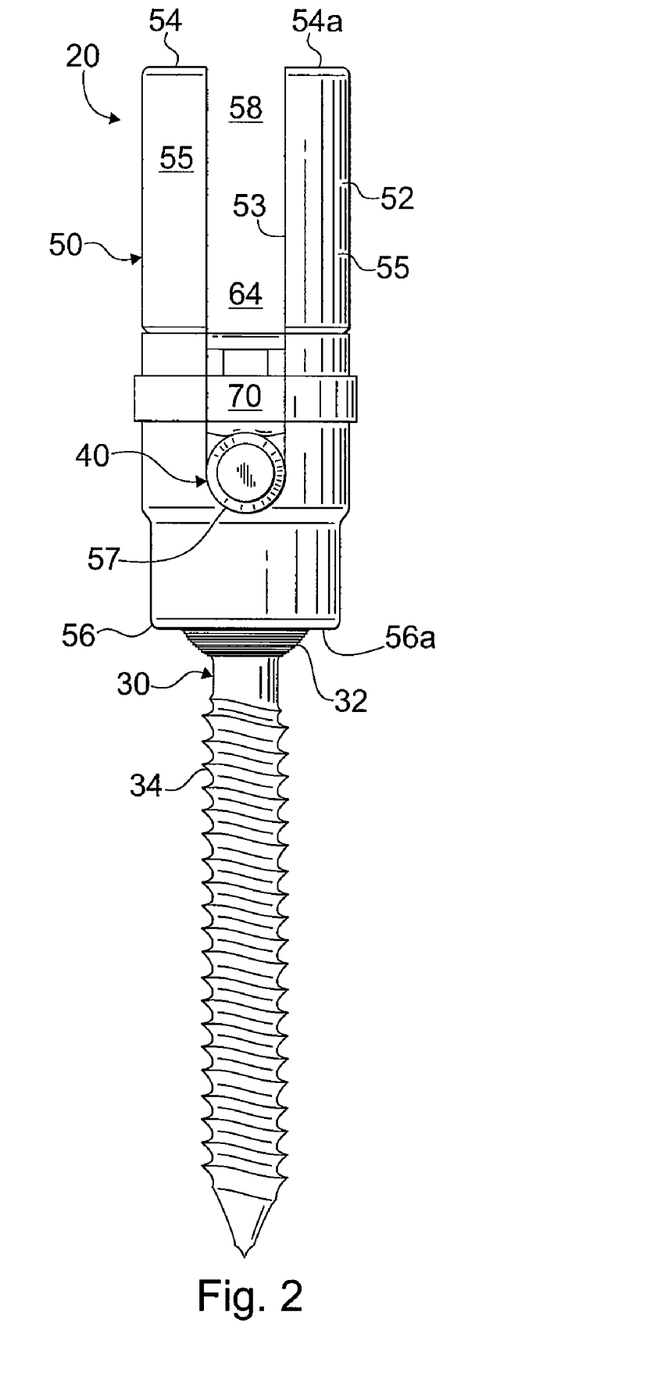
FIG. 2 is a perspective view of the screw and rod fixation assembly of FIG. 1, viewed from a second perspective.

Referring to the drawing figures generally, and to FIGS. 1 and 2 in particular, a fixation assembly 20 in accordance with an exemplary embodiment of the invention is shown. Fixation assembly 20 includes a polyaxial screw 30 and a hollow receiver component 50. Polyaxial screw 30 has a screw head 32 that is seated inside the receiver component 50, and a threaded shank 34 that projects outside the receiver component. Receiver component 50 supports a rod 40 that may be coupled to two or more polyaxial screws for stabilizing and correcting the spine at multiple levels and locations. Rod 40 is secured in receiver component 50 by a locking mechanism 70. As will be described in more detail below, locking mechanism 70 allows rod 40 to be is locked securely and efficiently in receiver 50 without application of any torque or countertorque on the assembly. In addition, locking mechanism 70 allows rod 40 to be secured in multiple locked stages without application of any torque or countertorque on the assembly.

Locking mechanism 70 rigidly secures polyaxial screw 30, rod 40 and receiver 50 together. A significant feature of locking mechanism 70 is its ability to be secured in receiver 50 without application of any torque. Another benefit of locking mechanism 70 is its ability to absorb radial stresses during insertion into receiver 50, minimizing the potential for radial splaying of the receiver. Still another benefit of locking mechanism is its ability to be released or unlocked from assembly 20. These and other advantages will become more apparent in the following sections.

Fixation assembly 20 and its components are compatible with a variety of components that exist in the marketplace, making the assembly and its components advantageous in that they can be used to upgrade or replace existing assemblies and components. Upgrading and/or replacement can be implemented before, during or after an existing fixation system is installed. By way of example only, fixation assembly 20 may be used with components shown and described in the '068 Patent discussed above, as well as U.S. Publication No. 2004/0193160 A1 to Richelsoph, U.S. Publication No. 2004/0162560 A1 to Raynor et al., U.S. Publication No. 2006/0149241 A1 to Richelsoph, and U.S. Publication No. 2006/0149233 to Richelsoph, the contents of which are incorporated by reference herein in their entireties.

The components of fixation assembly 20 will now be described in greater detail, with the continued understanding that the described features are merely exemplary, and are not intended to preclude other configurations from being used in accordance with the invention. Referring to FIG. 2, receiver 50 includes a hollow cylindrical body 52 having a top end 54 and a bottom end 56. Body 52 forms a central passage or bore 58 that extends between top and bottom ends 54, 56. Top end 54 includes a generally circular top opening 54a, and bottom end 56 similarly includes a generally circular bottom opening 56a.

A pair of diametrically opposed U-shaped channels 53 extend longitudinally along body 52 from top end 54 toward bottom end 56, stopping short of the bottom end. Each U-shaped channel 53 includes a rounded end 57 near bottom end 56 of receiver 50. U-shaped channels 53 are aligned with one another and form a conduit 64 extending transversely through bore 58. The width of conduit 64, and the curvature of rounded ends 57 of U-shaped channels 53, preferably conform with the dimensions and curvature of rod 40. U-shaped channels 53 are separated from one another by a pair of arms 55.

Bore 58 of receiver 50 is adapted to receive polyaxial screw 30 via an axial insertion. In a preferred embodiment, receiver 50 is a "top loaded" component. That is, the polyaxial screw and other components are inserted into receiver 50 through top opening 54a and advanced into bore 58. It will be understood that the direction in which components are loaded into receiver 50 is not entirely critical, and bottom loading arrangements are also possible and anticipated within the scope of the invention. For purposes of description only, a top loaded assembly will be described.

Figure 3:
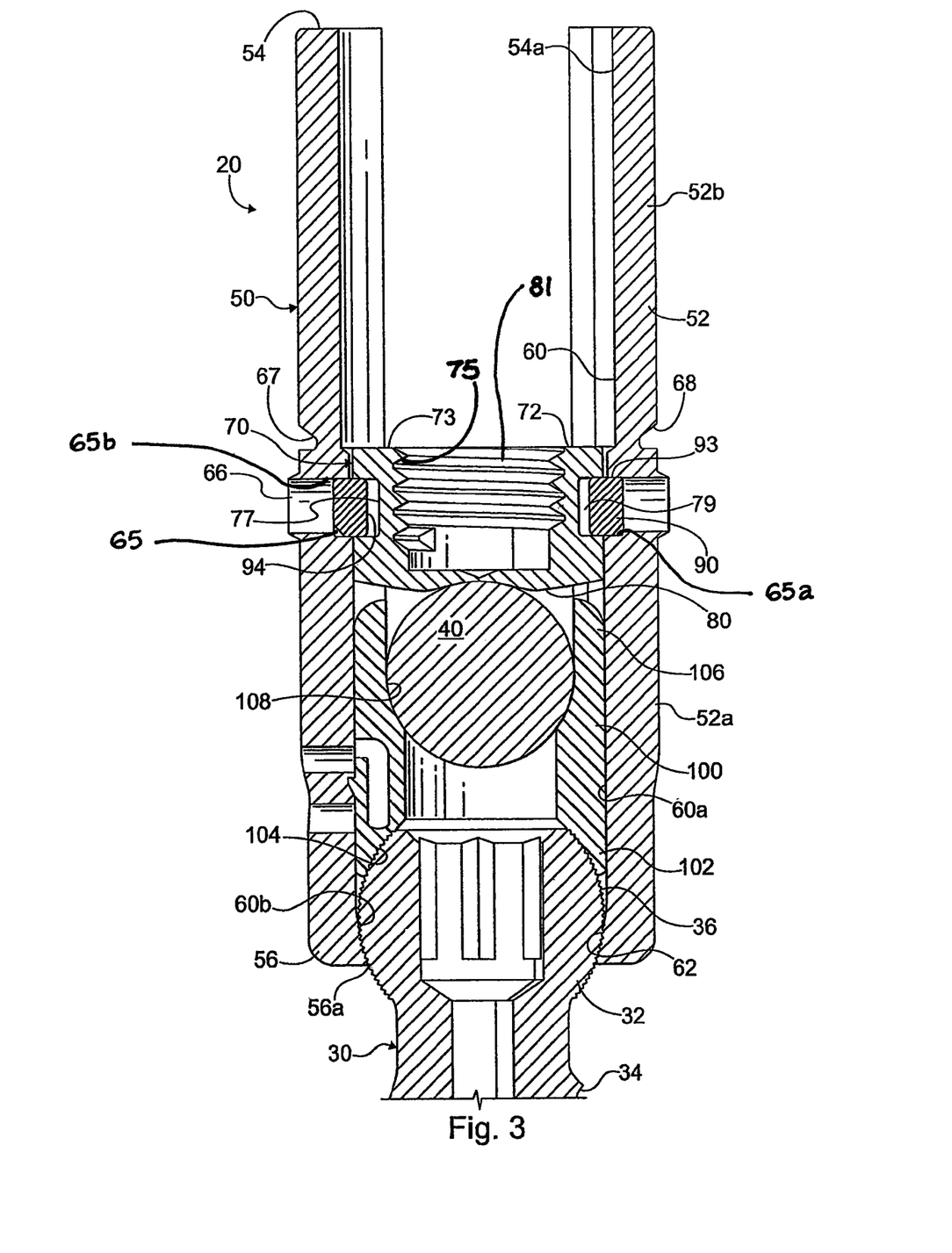
FIG. 3 is a partial cross-sectional view of the screw and rod fixation assembly of FIG. 1, taken through line 3-3 in FIG. 1, with the components shown in a locked condition.
Figure 4:
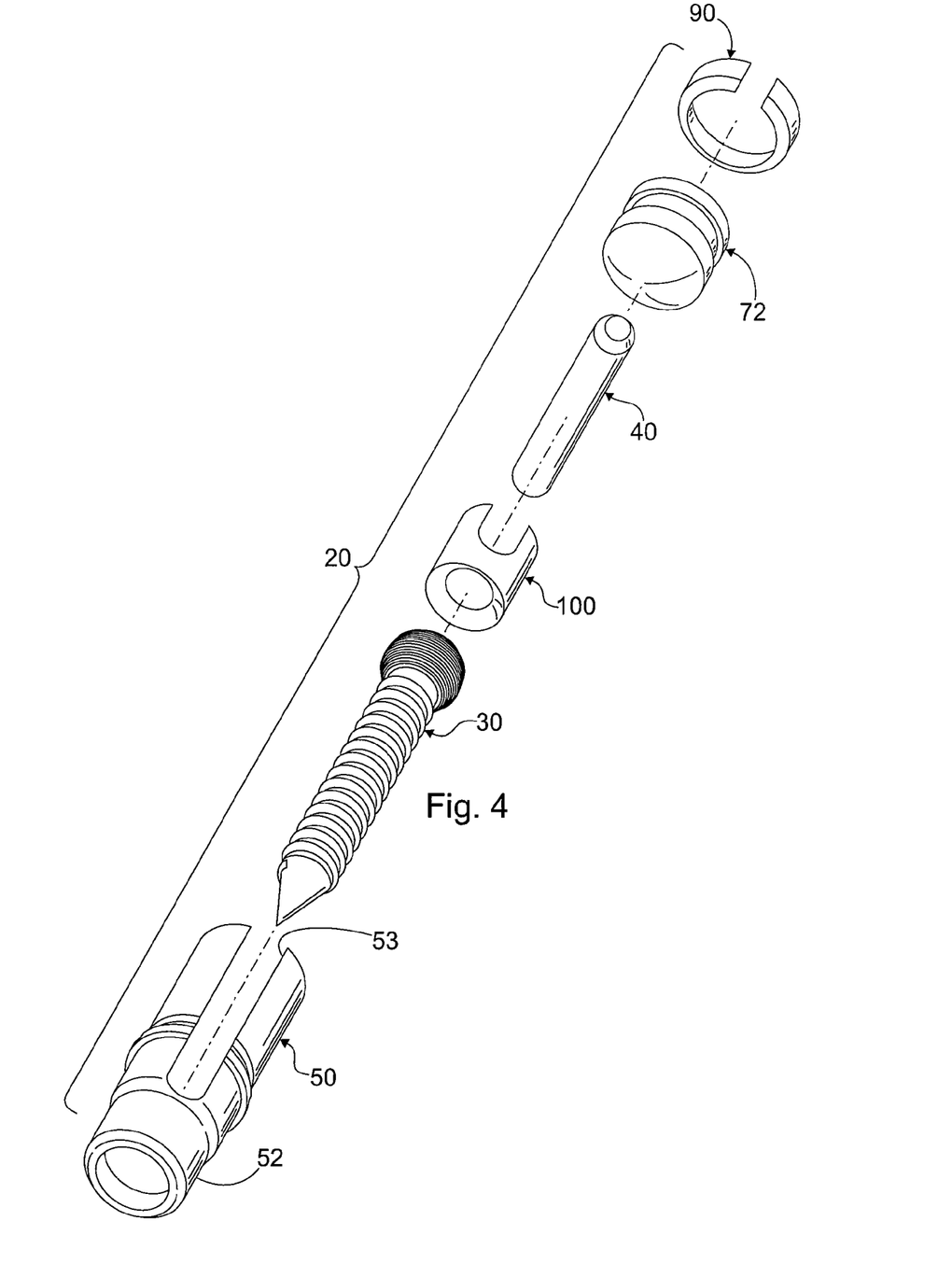
FIG. 4 is an exploded isometric view of the screw and rod fixation assembly of FIG. 1.

Referring now to FIG. 3, bore 58 is preferably cylindrical in shape like the receiver body 52, and is surrounded by an inner wall 60. Inner wall 60 permits passage of polyaxial screw 30 through bore 58, and more specifically, passage of polyaxial screw head 32. Preferably, the diameter of bore 58 is slightly larger than the maximum dimension of screw head 32 along a majority of the length of the bore. Inner wall 60 converges radially inwardly toward bottom end 56 so that bore 50 becomes slightly constricted at or near the bottom end. The restricted portion of bore 50 has a diameter that is less than the maximum dimension of screw head 32. In this arrangement, inner wall 60 forms a seat 62 that prevents passage of screw head 32 out of bottom end 56.

Inner wall 60 may be configured a number of ways to form seat 62. For example, inner wall 60 may be tapered radially inwardly in a conical taper. In the illustrated embodiment, inner wall 60 transitions from a generally straight cylindrical geometry 60a to a spherically contoured section 60b that lies adjacent to opening 56a at bottom end 56. Opening 56a has a diameter that is greater than the maximum diameter of screw shank 34 but less than the maximum dimension of screw head 32. Therefore, opening 56a permits passage of screw shank 34 and a portion of screw head 32, but prevents the entire screw head from passing through the opening.

In a preferred embodiment, a rod receiving insert 100 is inserted into bore 58, immediately adjacent or above screw head 32, to strengthen the interconnection between polyaxial screw 30, rod 40 and receiver component 50. A number of axial inserts may be used in accordance with the invention, and are described in several references including but not limited to the '068 Patent, U.S. Publication No. 2004/0193160 A1 to Richelsoph, and U.S. Publication No. 2006/0149241 A1 to Richelsoph, the contents of which are incorporated by reference herein in their entireties, as noted above. Insert 100 includes a bottom end 102 oriented toward bottom end 56 of receiver 50, and a top end 106 oriented toward top end 54 of the receiver. Bottom end 102 of insert 100 includes a recess 104 that receives a portion of screw head 32. Top end 106 of insert 100 includes a U-shaped rod receiving channel 108 that supports rod 40. In this arrangement, axial forces exerted on rod 40 to secure the rod in receiver 50 are transferred to insert 100 and screw head 32. Under such conditions, screw head 32 is compressed between insert 100 and seat 62.

As noted above, locking mechanism 70 rigidly secures polyaxial screw 30, rod 40 and receiver body 52 together. Locking mechanism 70 is axially inserted into bore 58 through open top end 54 of receiver 50. Although locking mechanism 70 can rotate in bore 58 during insertion and advancement into bore 58, rotation is not necessary to advance or tighten the locking mechanism into the bore. Locking mechanism 70 can include a variety of configurations for securing rod 40 in receiver 50.

Figure 5:
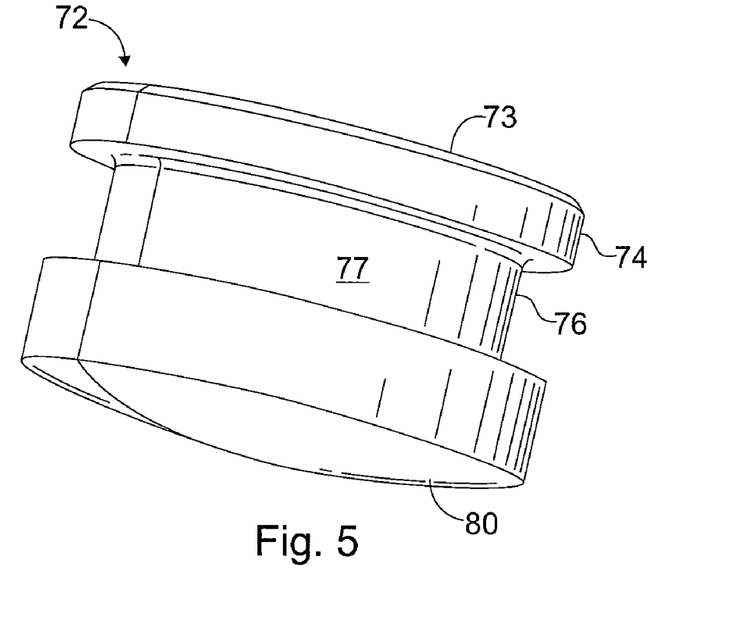
FIG. 5 is a perspective view of a first locking component in accordance with the present invention.
Figure 6:
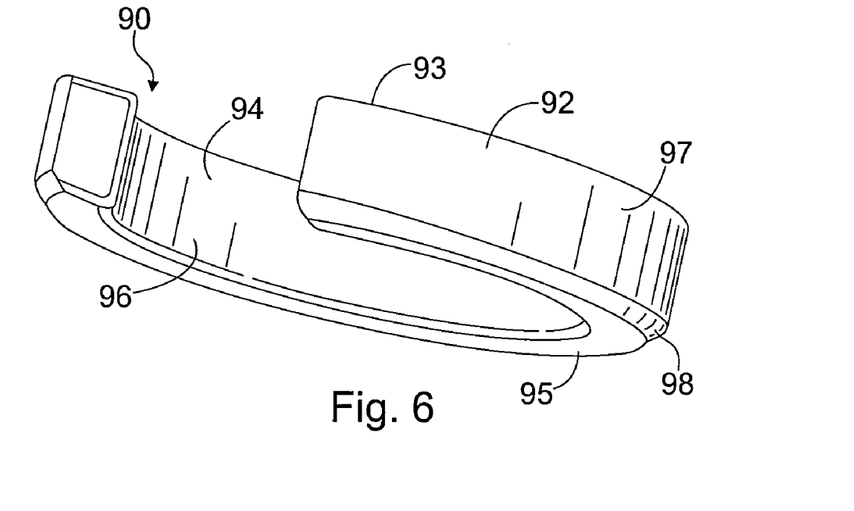
FIG. 6 is a perspective view of a first locking element in accordance with the present invention.

Referring now to FIG. 5, locking device 70 includes a generally cylindrical cap 72. Cap 72 includes a tool engaging end 73, an outer wall 74 and a rod engaging end 80. Outer wall 74 has a generally smooth surface and includes an annular recess 76 that extends radially inwardly in cap 72, terminating at an end wall 77. The diameter of outer wall 74 is slightly less than the diameter of bore 58. As will be described in subsequent sections, this arrangement allows locking mechanism 70 to be axially advanced into bore 58. Locking device 70 also includes a locking element that cooperates with cap 72. One example of a locking element is shown in the form of a locking ring 90 in FIG. 6. Locking ring 90 has a C-shaped ring body 92 formed of a resilient flexible material. C-shaped ring body 92 includes an inner face 94 and an outer face 97. Locking ring 90 forms a segment of a circle, or arc, that includes an central open section 96 surrounded by inner face 94.

Figure 7:
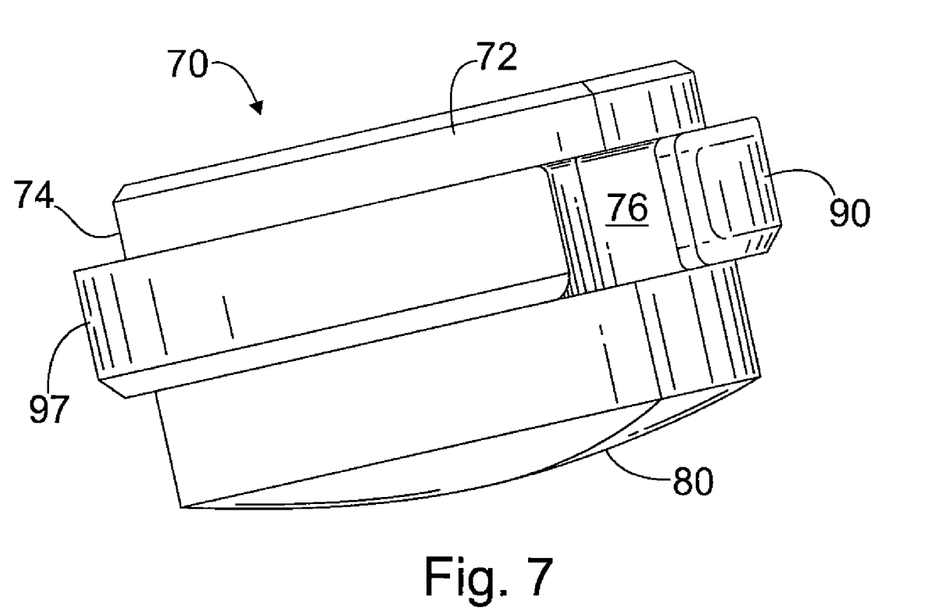
FIG. 7 is a perspective view of the first locking component of FIG. 5 and the first locking element of FIG. 6, shown in an assembled condition.

Referring to FIG. 7, locking mechanism 70 is shown with cap 72 and locking ring 90 in an assembled condition. Central opening 96 of locking ring 90 is sufficiently large to allow the locking ring to fit around the circumference of cap 72 and inside recess 76. When locking ring 90 is in a relaxed condition, an inner portion of the locking ring extends within recess 76, and an outer portion projects radially outwardly from the recess and outer wall 74 of cap 72. A small radial clearance 79 is maintained between inner face 94 and end wall 77 in groove, as shown in FIG. 3.

Locking ring 90 is radially deformable to lock and unlock locking mechanism 70 inside receiver 50. More specifically, C-shaped body 92 is elastically expandable and compressible within recess 76 so that a portion of locking ring 90 can engage with and disengage from inner wall 60 of receiver 50. C-shaped body 92 is deformable between a radially compressed condition and a radially expanded condition. In the compressed condition, locking ring 90 is pressed inwardly into recess 76, assuming a smaller diameter. In the expanded condition, locking ring 90 is extends outwardly, assuming a larger diameter. Upon being compressed, locking ring 90 stores energy that biases C-shaped body 92 radially outwardly toward a relaxed state. Locking ring 90 exhibits an outwardly directed spring bias upon being compressed, and exhibits a small amount of resistance to radial compression.

Locking ring 90 may be stretched or pulled outwardly from the relaxed state. For example, locking ring 90 may be stretched outwardly to fit the C-shaped body around the recess portion 76 of cap 72. Preferably, the material of locking ring 90 has shape memory and resilience. In this arrangement, locking ring 90 returns more or less to its original configuration when stretching force is released and the locking ring returns to the relaxed state. At least a portion of C-shaped body 92 preferably extends into recess when locking ring 90 is in the relaxed condition, so that the locking ring does not slip off cap 72.

Locking ring 90 is sufficiently flexible to compress and expand in response to engagement with inner wall 60 of bore 58 when the locking ring is inserted into receiver 50. For example, locking ring 90 is sufficiently flexible to compress inwardly in response to contacting narrow sections of bore 60. Locking ring 90 is also sufficiently resilient to expand as it aligns with wider sections of bore 60. When locking ring 90 aligns with sections of bore 60 that have a larger diameter than the diameter of the locking ring in the relaxed state, or when the locking ring is not otherwise restrained by inner wall 60, the locking ring expands within bore 58 until it reaches its relaxed state.

Locking mechanism 70 preferably incorporates a surface contour that assists in radial compression of the locking element in bore 58. Referring again to FIG. 6, locking ring 90 has a generally flat top end 93 and a contoured bottom end 95. Contoured bottom end 95 is angled with respect to the direction of axial movement so that when the bottom end contacts a constriction in bore 58, a radial component of force, i.e. a force parallel to the plane of locking ring 90, is directed into the locking ring. In this configuration, locking ring 90 will be compressed radially inwardly in response to contact with a narrow constriction in inner wall 60. A variety of contours and profiles may be used on the bottom of the locking element for this purpose. Bottom end 95 of locking ring 90 includes a beveled or chamfered edge 98 that forms an acute angle with outer face 97. It will be understood that other geometries can be used within the scope of the invention to direct a radial component of force into locking element, including but not limited to rounded edges between the bottom end and outer face, or an outer face with a diameter that gradually decreases or tapers from the top end toward the bottom end.

Figure 8:
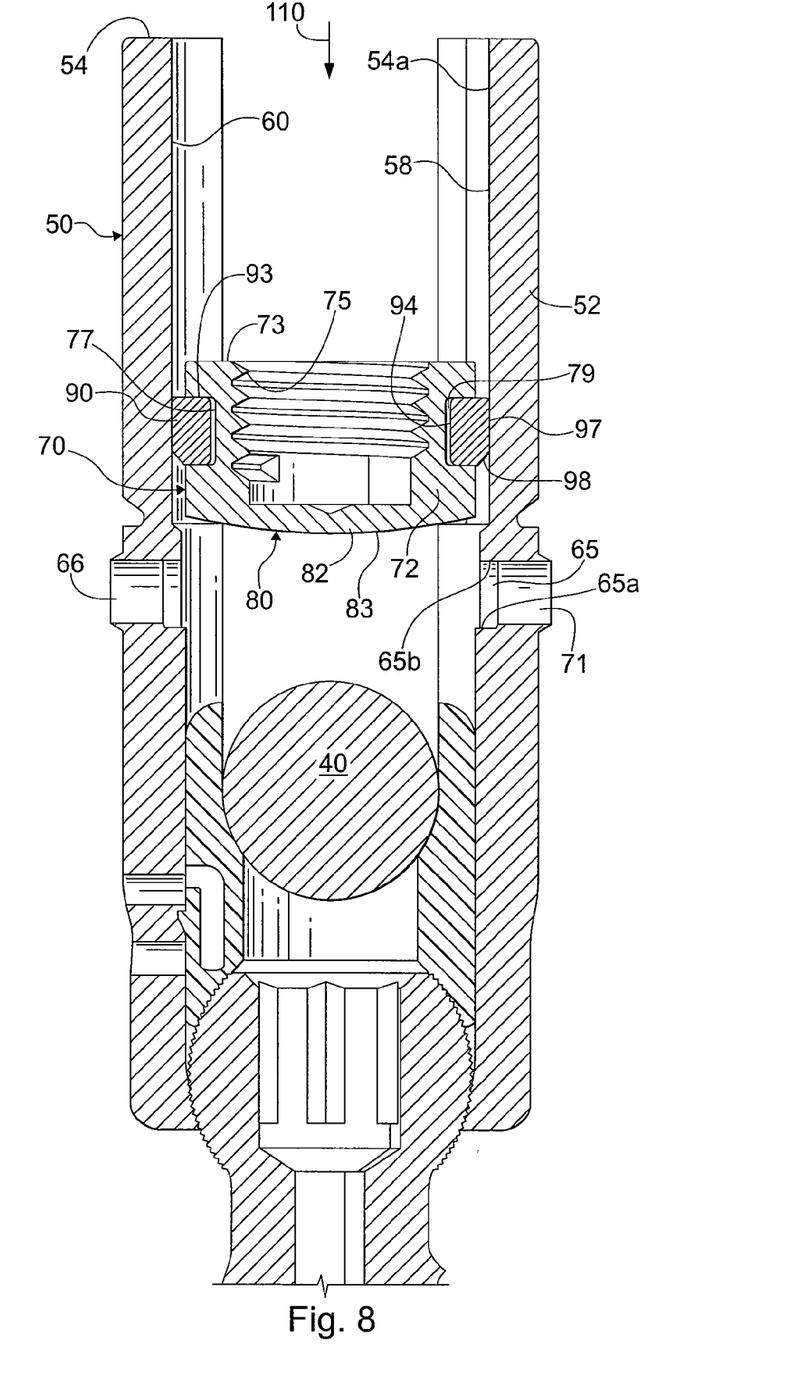
FIG. 8 is a partial cross-sectional view of the screw and rod fixation is assembly components of FIG. 3, with the components shown in an unlocked condition.

Referring now to FIG. 8, the manner in which locking device 70 operates will be described. Locking element 70 is initially loaded through top opening 54a and advanced axially into bore 58 of receiver 50. The direction of axial insertion is represented by arrow 110 in FIG. 8. In a preferred embodiment, the diameter of top opening 54a and bore 58 are slightly smaller than the outer diameter of locking ring 90 when the locking ring is in a relaxed condition. When locking ring 90 is inserted into top opening 54a, the peripheral edge surrounding the top opening engages chamfered edge 98, compressing locking ring 90 radially inwardly against the spring bias. As locking ring 90 is compressed, outer face 97 is pressed radially inwardly, reducing the outer diameter or dimension of the locking ring. In addition, inner face 94 converges radially inwardly toward end wall 77 in recess 96. The radial clearance 79 in recess 96 is sufficient to receive at least a portion of locking ring 90 as the locking ring is compressed. Locking ring 90 is compressed until the diameter at outer face 97 is small enough to pass through top opening 54a into bore 58.

Energy is stored in locking ring 90 as the locking ring is compressed, biasing the locking ring radially outwardly toward its expanded state. Because the diameter of bore 58 near top opening 54a is smaller than the diameter of locking ring 90 in the relaxed state, the locking ring remains under compression as it is advanced into the bore. The outward spring bias of locking ring 90 maintains outer face 97 in constant contact with inner wall 60 during advancement, keeping the locking device centered in the bore. In this condition, which is shown in FIG. 8, locking device 70 is axially advanced in bore 58 with the outer face 97 slidably engaging inner wall 60 of the bore.

Receiver 50 includes an annular groove 65 having an axial dimension or width that is slightly larger than the axial dimension or width of locking ring 90. As locking device 70 is axially advanced into alignment with groove 65, locking ring 90 is no longer compressed or restrained at the same radial location. Locking ring 90 is free to expand under the spring bias toward the relaxed condition. In such an event, locking ring 90 springs outwardly until an outer portion of the locking ring rests inside groove 65, as shown in FIG. 3. The flat top end 93 of locking ring 90 is axially aligned with a top wall 65b of groove 65, forming an obstruction that prevents locking device 70 from being axially withdrawn from bore 58. In this condition, locking device 70 locks the axial position of rod 40 in receiver 50.

Unlike known locking mechanisms, locking device 70 does not cause radial splaying of the arms 55 as it is advanced into bore 58. The term "splaying" includes but is not limited to instances where a locking mechanism pushes the walls of the receiving member radially outwardly as it is advanced into the bore. Splaying can cause damage or weakness in the receiver body, and compromise the integrity of the receiver body's engagement with the polyaxial screw head. Severe splaying also impacts the engagement between the locking device and inner wall of the receiver, which can be especially problematic for threaded locking mechanisms. When a threaded locking mechanism becomes disengaged from the inner wall of the receiver, the locking mechanism becomes inoperable and can no longer securely lock the rod in place.

Locking mechanism 70 avoids problems associated with the "wedge effect" by absorbing radial stresses that are created as the locking mechanism is advanced into bore 58. As noted above, locking element 90 is radially compressible in response to contact with inner wall 60 of bore 58. Rather than splaying the arms 55 of receiver 50 outwardly to facilitate passage through the bore, locking element 90 yields to the inner wall 60 and contracts radially inwardly as it passes through constrictions or sections of the bore having a smaller diameter than the locking element. Arms 55 are not subject to any significant outward stress, eliminating the potential for splaying. Because splaying of arms 55 is substantially prevented, there is no need for external reinforcements on receiver body 50, such as external lock nuts or other braces that prevent outward displacement of the arms.

Referring again to FIG. 8, cap 72 has a tool engaging end 73 and a socket 75. Socket 75 is adapted to receive and engage an insertion tool through tool engaging end 73. A variety of socket shapes and configurations may be used for connection with an insertion tool, including but not limited to standard sized hexagonal sockets. In FIG. 3, socket 75 is surrounded by a threaded surface 81 for mating with a threaded surface on an insertion tool. Socket 75 does not extend partially through cap 72, stopping just before reaching rod engaging end 80. In this arrangement, a thin wall 82 is formed at rod engaging end 80.

Thin wall 82 of rod engaging end assists in locking down rod 40 in receiver body 50. In a preferred embodiment, thin wall 82 is formed of a resilient flexible material that forms a spring element at rod engaging portion 80 of cap 72. The exterior of thin wall 82 includes a convex outer surface 83. Convex surface 83 engages rod 40 when locking device 70 is set in a locked condition. Thin wall 82 is adapted to flex with elastic deformation when cap 72 is advanced into contact with rod 40. Rod 40 may also exhibit elastic deformation. Depending on the materials used and other variables, thin wall 82 and rod 40 may also exhibit plastic deformation when the rod is locked down by the locking device 70.

The thin wall 82 and rod engaging end 80 operate in the following manner to assist locking of rod 40. Locking mechanism 70 is advanced into bore 58 by axial force applied by an insertion tool. Locking mechanism 70 is advanced until rod engaging end 80 of cap 72 contacts rod 40. After rod engaging end 80 contacts rod 40, continued advancement of locking mechanism 70 will press convex surface 83 against the rod. Pressure against thin wall 82 eventually reaches a threshold limit, at which point the thin wall flexes inwardly into socket 75 under elastic deformation. When thin wall 82 elastically deforms, elastic energy is stored at rod engaging end 80. The resiliency of thin wall 82 creates a restoring force to return the thin wall to its initial convex shape. This restoring force is opposed, at least initially, by the axial force exerted by the insertion tool.

Rod engaging end 80 preferably contacts rod 40 just before locking ring 90 aligns with groove 65 in bore 58. In this arrangement, thin wall 82 will undergo elastic deformation and store energy prior to the point where locking ring 90 aligns with groove 65 and snaps outwardly into a locked condition. Once locking ring 90 snaps into groove 65, further advancement of locking device 70 is limited by the abutment between locking ring 90 and a lower wall 65a within groove 65. Axial force is released from the insertion tool, so that the restoring force in thin wall 82 is no longer suppressed. The stored energy in thin wall 82 is released to return the thin wall to its original shape prior to elastic deformation. Restoring force is exerted against rod 40, which is fixed in position relative to receiver 50. Because rod 40 does not move, the restoring force has the effect of biasing the locking mechanism 70 upwardly, or in the direction opposite the rod.

The biasing force on locking mechanism 70 pushes the expanded locking ring against an upper wall 65b of groove 65. In particular, top end 93 of locking ring 90 bears against upper wall 65b of groove. This prevents locking mechanism 70 from advancing any further toward top end 54 of receiver 50. Groove 65 is preferably arranged relative to locking device 70 such that locking ring 90 abuts the upper wall 65a of groove while thin wall 82 is still in an elastically deformed state. That is, the locking ring 90 preferably abuts upper groove wall 65a before thin wall 82 can fully return to its original convex shape. Because thin wall 82 is left in an elastically deformed condition, thin wall provides a residual biasing force against locking device 70 that rigidly secures the locking device in place.

As noted above, thin wall 82 preferably undergoes some elastic deformation prior to the point where locking ring 90 aligns with groove 65 and snaps outwardly into a locked condition. This provides an upward biasing force against locking device 70, which is created by the restoring force in thin wall 82. Thin wall 82 thus acts like a spring member that pushes and holds locking device 70 in a locked position. The amount of elastic deformation in thin wall 82, and the amount of upward biasing force, may be controlled by adjusting a number of parameters including but not limited the material of cap 72, the thickness of thin wall 82, and the axial distance between the rod-cap interface and upper wall of groove 65.

The locking device 70 will provide secure locking engagement without an upward biasing force. That is, the engagement between locking ring 90 and upper wall 65a of groove 65 is sufficient to lock rod 40 against upward displacement, without the upward biasing force. Nonetheless, providing an upward biasing force against locking device 70 will enhance the locking engagement between locking device 70 and receiver 50. Therefore, it is preferred to provide at least some upward spring force against the locking device 70. The spring force created by rod engaging end 80 is also desirable to compensate for manufacturing tolerances.

Locking mechanism 70 is advantageous in that it provides the option of a releasable lock. As with the locking operation, the procedure for releasing or unlocking the lock is accomplished without the application of torque. The lock can be taken out of the locked condition by radially compressing locking ring 90 until the ring's outer face 97 no longer extends in groove 65. A variety of configurations may be used to provide the releasable lock. Referring to FIGS. 1 and 8, receiver body 52 includes a pair of diametrically opposed release apertures 66. Each release aperture 66 is axially aligned with groove 65 and extends through the wall of receiver 50 to form an passage 71 with groove 65. In this arrangement, passages 71 provide access to locking ring 90 from the exterior of receiver 50 when the locking ring is locked in groove 65.

Passages 71 have dimensions that allow insertion and manipulation of a release tool, which is used to radially compress and unlock locking ring 90. A variety of unlocking instruments for radially compressing locking ring 90 can be imagined. For example, a tweezers-type instrument with a pair of scissor handles on one end, and an opposing pair of inwardly-facing prongs on the other end may be used. The prongs have cross-sectional dimensions that are smaller than the dimensions of apertures 66 and passages 71, and are longer than the length of the passages. The ends of the prongs can be inserted into apertures 71 and placed into contact with outer face 97 of locking ring 90. Locking ring 90 can be unlocked by inserting the prongs of the instrument into release apertures 66 so as to contact outer face 97 of locking ring 90, and squeezing the handles together to converge the ends of the prongs toward one another. The ends of the prongs apply radially inward forces against outer face 97 to radially compress locking ring 90. Radial compression is applied to locking ring 90 until the entire ring is moved out of groove 65. In this condition, the locking device 70 is unlocked or released. Locking device 70 can thereafter be axially displaced in bore 58 toward top end 54 of receiver 50, such as by engagement with a removal instrument inserted into socket 75 of cap 72, and removed from the receiver.

Figure 14:
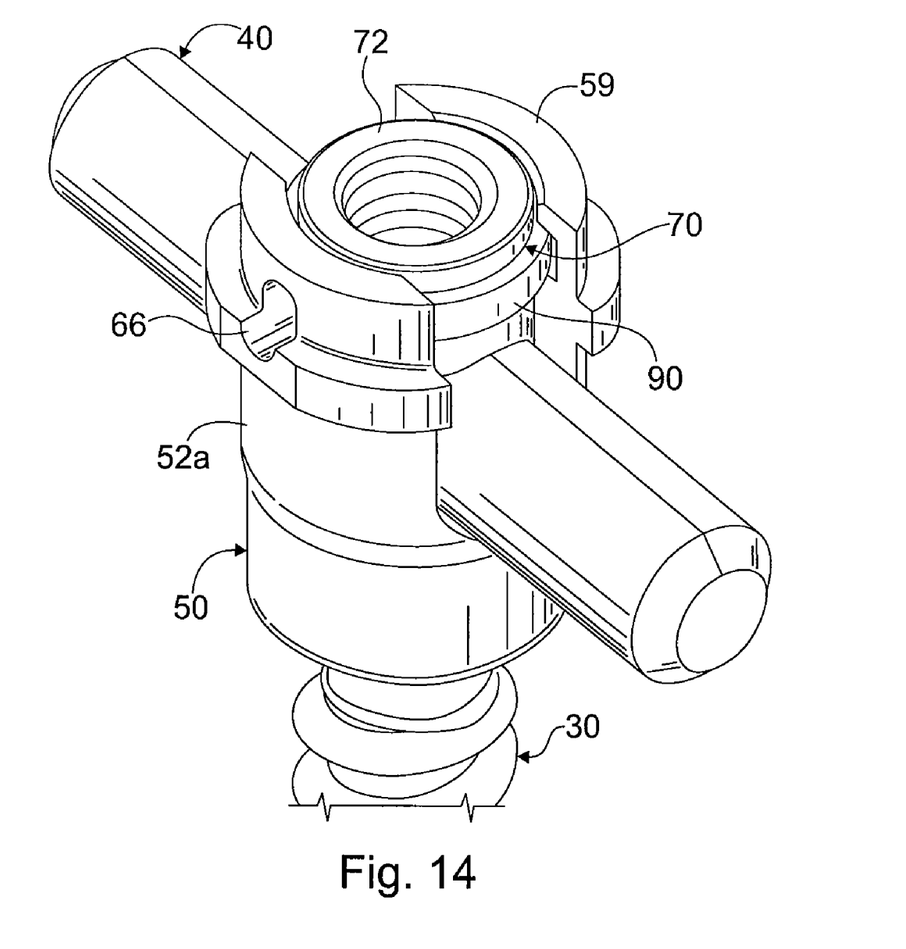
FIG. 14 is a partial perspective view of a screw and rod fixation assembly in accordance with the present invention, after a break-off portion of the assembly is removed.

In a rod reduction procedure, receiver 50 should remain relatively stable to facilitate insertion of rod 40 into bore 58. Therefore, receiver 50 preferably includes a long body 52 so that reduction instruments can securely engage receiver 50. After rod 40 is secured in its final position, the long body is no longer necessary, and may be undesirable. Rod 40 and locking device 70 are compact enough to fit within a lower portion of receiver 50, requiring only a fraction of the total length of receiver body 52. Therefore, receiver 50 preferably includes one or more thinned portions, such as thinned section 67 in FIG. 3, that allows a portion of receiver body 52 to be broken away after the rod is secured, if desired. Thinned section 67 may be configured in a number of ways to make the receiver body 52 easily breakable. In FIG. 3, thinned section 67 has a circumferential groove 68 that divides receiver body 52 into a base portion 52a below the groove, and a break-away portion 52b above the groove. In this arrangement, break-away portion 52b can be removed from receiver 50 after rod 40 has been locked. Preferably, thinned section 67 is axially positioned within a plane more or less aligned with the top end of locking device 70 when the locking device is secured in the locked position. Referring now to FIG. 14, receiver 50 is shown with the upper portion 52b removed. Lower portion 52a of receiver body 52 remains in place, with a broken edge 59 more or less coplanar with the top of locking device 70.

Referring now to FIGS. 9-12, an alternate embodiment of a locking device 170 is shown in accordance with the present invention. Many of the features shown in locking device 170 are identical to the features of locking device 70, and therefore will not be discussed. In contrast to locking device 70 described above, locking device 170 utilizes a three-component assembly comprising of a cap 172, a locking ring 190 and a spring element 182. Cap 172 has a hollow and generally cylindrical body with a rod engaging end 180. Rod engaging end 180 forms a hollow receptacle 185 for receiving spring element 182. Spring element 182 is disc-shaped and has a diameter more or less equal to the diameter of the receptacle. Rod engaging end 180 further includes a lip 187 that wraps around a bottom portion of spring element 182 to retain the spring element inside receptacle 185.

Spring element 182 is similar to thin wall 82 in that it is formed of a resilient flexible material and includes a convex outer surface 183. Convex surface 183 engages a rod when locking device 170 is set in a locked condition. Spring element 182 is adapted to flex with elastic deformation when cap 172 is advanced into contact with a rod. The resiliency of spring element 182 creates an upward biasing force against locking device 170 in the locked condition that rigidly secures the locking device in place. A number of components can be used as the spring element, including but not limited to a solid disc or Belleville washer.

Figure 9:
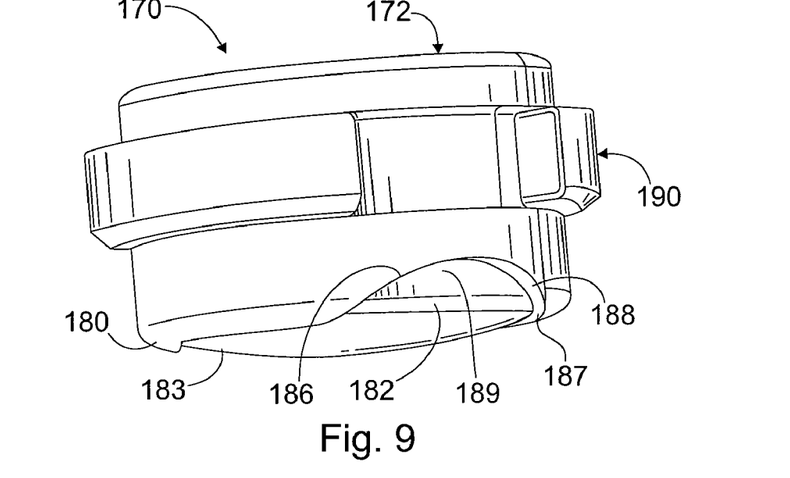
FIG. 9 is a perspective view of a second locking component in accordance with the present invention, shown in an assembled condition with the first locking element of FIG. 6.
Figure 10:
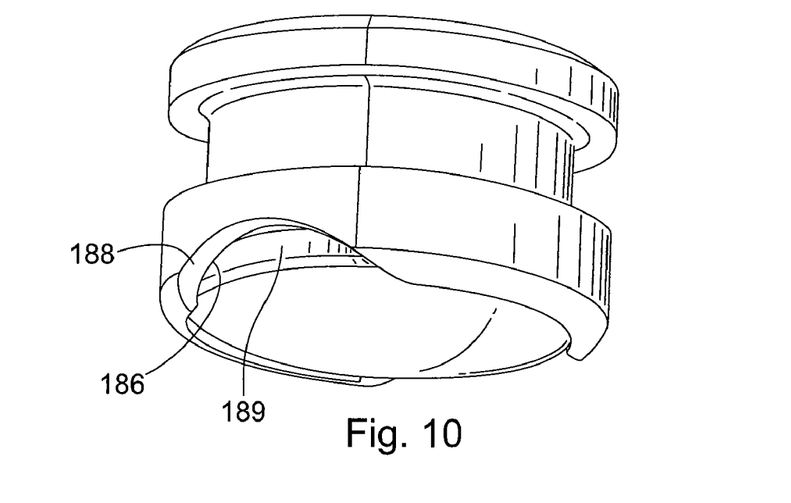
FIG. 10 is a perspective view of the second locking component of FIG. 9.
Figure 11:
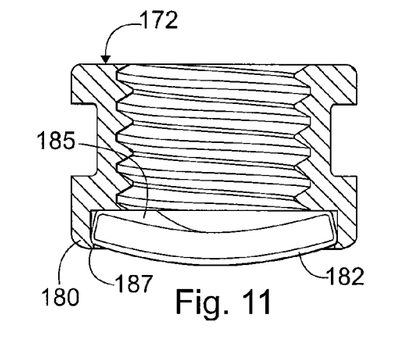
FIG. 11 is a cross-sectional view of the second locking component of FIG. 9.
Figure 12:
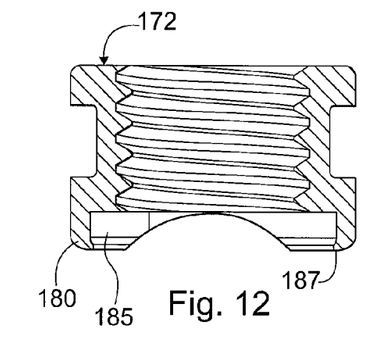
FIG. 12 is a cross-sectional view of the second locking component of FIG. 9, with a bottom part removed for clarity.

Outer convex surface 183 is recessed inside receptacle 185, with only a portion projecting out beyond lip portion 187. Rod engaging end 180 preferably includes a contoured portion to enhance the engagement between locking device 170 and the rod. In FIGS. 9 and 10, cap 172 includes a pair of diametrically opposed notches or cutouts 186 at rod engaging end 180. Each notch 186 has a generally circular profile or contour, forming a rounded edge 188. Notches 186 form an inverted channel 189 that receives the rod when outer convex surface 183 deflects. Inverted channel 189 provides a seat for the upper portion of the rod, enhancing the stability and rigidity of the locking device. The radius of rounded edges 188 is more or less equal to the radius of the rod being secured. In this arrangement, rod engaging end 180 of locking device 170 conforms to and mates with the rod's exterior, further securing the components against rotation relative to one another.

Figure 13:
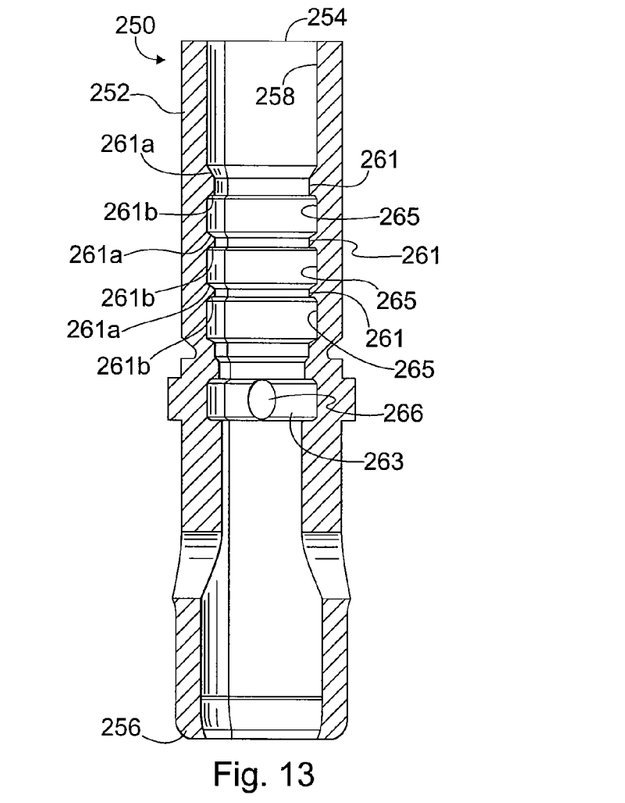
FIG. 13 is a cross-sectional view of a rod receiving component in accordance with the present invention.

Referring now to FIG. 13, a receiver 250 is shown in cross section in accordance with another exemplary embodiment. Receiver 250 is configured to permit locking of the rod in multiple positions or stages of reduction. Receiver 250 includes a generally cylindrical body 252 forming an elongated bore 258. Body 252 has an open top end 254 for receiving a locking device, such as the devices described herein. Receiver body 252 also includes an open bottom end 256 through which a portion of a fixation screw can extend. Bore 258 has a series of annular grooves 265 each defining a separate chamber for receiving a locking element, such as locking ring 90. Each groove 265 lies axially adjacent to a constriction 261. Each constriction 261 includes an annular chamfered or beveled edge 261a that forms an acute angle with the axis of receiver 250. In addition, each constriction 261 includes an edge 261b that lies generally perpendicular to the axis of receiver 250.

As locking device is advanced into receiver 250, beveled edge 261a assists in the axial progression of the locking device from a wider portion of bore 258 to a narrower portion of bore. Beveled edge 261 directs a radial component of force into the locking ring to radially compress and contract the locking ring so that the outer face of the locking ring can pass through each constriction. Once locking ring passes the constriction 261, the locking ring snaps outwardly to a locked condition, in the manner discussed previously. Perpendicular edge 261b of the constriction 261 that lies above the locking ring abuts the top end of the locking ring to prevent the locking device from moving back toward the top of receiver 250. A final locking recess 263 is aligned with a release aperture 266 to allow unlocking of the device, if desired.

Embodiments of the present invention may include a number of optional features to strengthen the locking engagement between the various components. In a preferred embodiment, for example, the exterior surface of the polyaxial screw head 32 may include a plurality of ridges 36, as shown for example in FIG. 3, to enhance the gripping engagement between the screw head and the interior of receiver 50, and the engagement between the screw head and the concave portion of insert 100. The components of the assembly may be manufactured from several different implant grade materials, including but not limited to a variety of alloys and synthetic materials. For example, cap 72 and locking ring 90 can be manufactured from cobalt chrome, and screw 30, rod 40 and insert 100 can be manufactured from titanium. The components of locking mechanisms 70, 170 may be made from the same materials or different materials. For example, cap 172 may be formed from titanium, and the spring element 182 and locking ring 190 may be manufactured from cobalt chrome. The same material may be selected for all the components, or only select components in a variety of possible combinations.

While preferred embodiments of the invention have been shown and described herein, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed is:

1. A locking mechanism for locking a rod in a screw and rod fixation assembly, the locking mechanism comprising:
a generally cylindrical cap, configured to apply a downward axial force on a rod, the cap having an external sidewall and an annular recess formed in the sidewall, the recess extending radially inwardly into the cap; and
a locking element movably disposed in the recess and circumscribing at least a portion of the cap, the locking element retained in a captive condition in the recess such that the cap encloses the locking element on two sides so the locking element cannot be removed from the recess, the locking element being radially deformable between a compressed condition, in which the locking element assumes a first cross-sectional dimension, and a relaxed condition, in which the locking element assumes a second cross-sectional dimension, the second cross-sectional dimension being larger than the first cross-sectional dimension.

2. The locking mechanism of claim 1, wherein the cap comprises a non-threaded exterior.

3. The locking mechanism of claim 1, wherein the cap comprises a rod engaging end having a convex face.

4. The locking mechanism of claim 3, wherein the rod engaging end comprises a Belleville washer recessed into the bottom of the cap.

5. The locking mechanism of claim 3, wherein the rod engaging end comprises a resiliently flexible spring surface.

6. The locking mechanism of claim 1, wherein the locking element comprises a first end face and a second end face arranged opposite the first end face, wherein the first end face is chamfered.

7. The locking mechanism of claim 1, wherein the locking element has a C-shaped body.

8. The locking mechanism of claim 1, wherein the cap comprises a tool engaging end having a socket.

9. The locking mechanism of claim 1, wherein the sidewall circumscribes at least a portion of the rod engaging end.

10. The locking mechanism of claim 9, wherein the sidewall includes diametrically-opposed notches, each having a rounded contour.

11. A spinal fixation assembly comprising:
a receiver for a spinal fixation rod, the receiver comprising a hollow tubular body having a bore and a locking surface in the bore;
a generally cylindrical locking cap in the bore of the receiver, the locking cap configured to apply a downward axial force on a rod, the locking cap having an external sidewall, an annular recess formed in the sidewall and extending radially inwardly into the cap, and a rod engaging end; and
a locking element circumscribing at least a portion of the cap and movably disposed in the recess, the locking element retained in a captive condition in the recess such that the cap encloses the locking element on two sides so the locking element cannot be removed from the recess, the locking element extending from the sidewall of the locking cap in engagement with the locking surface in the bore, the locking element being radially displaceable between a compressed condition and a relaxed condition, the locking element engaging the locking surface in the relaxed condition, fixing the axial position of the locking cap in the bore.

12. The spinal fixation assembly of claim 11, wherein the locking element comprises a locking ring surrounding at least a portion of the locking cap.

13. The spinal fixation assembly of claim 11, wherein the receiver comprises a locking element release aperture axially aligned with the locking element.

14. The spinal fixation assembly of claim 11, wherein the locking surface comprises a plurality of grooves incrementally spaced along the bore, the locking element extending into one of the grooves.

15. A method of locking a spinal fixation member in a receiver of a pedicle screw fixation assembly, the receiver having a longitudinal bore along its axis and a channel extending transversely to the bore, the method comprising the steps of:
   placing the spinal fixation member into the channel of the receiver;
   axially advancing a locking cap in the bore toward the spinal fixation member without application of any torque;
   and securing the locking cap in a locked position above the spinal fixation member without application of any torque,
   wherein the step of securing the locking cap comprises axially advancing the locking cap in the bore until a spring element on the locking cap axially aligns with a locking surface in the bore, and
   wherein the step of advancing the locking cap comprises the step of radially compressing the spring element as the locking cap is advanced axially in the bore.

16. The method of claim 15, wherein the step of securing the locking cap in a locked position comprises radially expanding the spring element into engagement with the locking surface as the spring element aligns axially with the locking surface.

17. The method of claim 15, wherein the locking surface comprises a plurality of annular recesses incrementally spaced along the bore.

18. The method of claim 17, wherein the step of securing the locking cap in a locked position comprises the steps of axially advancing the locking cap in the bore without rotation, radially compressing the spring element as the locking cap is advanced axially in the bore, radially expanding the spring element into a first recess as the spring element aligns with the first recess, advancing the locking cap further without rotation, radially compressing the spring element as the locking cap is further advanced axially in the bore, and radially expanding the spring element into a second recess as the spring element aligns with the second recess.

19. The method of claim 15, wherein the step of securing the locking cap in a locked position comprises advancing the locking cap until a bottom end of the locking cap contacts the spinal fixation member.

20. The method of claim 15, wherein the step of securing the locking cap in a locked position comprises the step of applying an upwardly directed biasing force on the locking cap.

21. The method of claim 20 wherein the step of applying an upwardly directed biasing force on the locking cap comprises the step of elastically deforming a portion of the locking cap to create stored energy in the locking cap.

* * * * *